United States Patent

Wylie et al.

[11] Patent Number: 5,950,674
[45] Date of Patent: Sep. 14, 1999

[54] FLUID CONTROL VALVE ARRANGEMENT

[75] Inventors: David A. Wylie, Unionville; Ori D. Raubvogel, North York, both of Canada

[73] Assignee: Perkin-Elmer (Canada) Ltd., Markham, Canada

[21] Appl. No.: 08/709,885

[22] Filed: Sep. 9, 1996

[51] Int. Cl.[6] .................................................. F16K 11/22
[52] U.S. Cl. .......................................... 137/597; 137/606
[58] Field of Search ...................................... 137/606, 597

[56] References Cited

U.S. PATENT DOCUMENTS

| | | | |
|---|---|---|---|
| 4,353,243 | 10/1982 | Martin | 73/23.1 |
| 4,773,446 | 9/1988 | Farnswoth et al. | 137/606 |
| 5,320,139 | 6/1994 | Paul et al. | 137/606 X |

*Primary Examiner*—Stephen M. Hepperle
*Attorney, Agent, or Firm*—Skjerven, Morrill, MacPherson, Franklin & Friel LLP; David E. Steuber

[57] ABSTRACT

A fluid control valve arrangement allowing very complex valve interconnection schemes to be implemented in a small volume is disclosed. The fluid control valve arrangement utilizes seat plates positioned above and below a block to allow creation of three layers of material between valve elements on opposite sides of the block. Since there are three layers of material between blister valve elements on opposite sides of the block, there are two interfaces on separate levels from those levels contacting valve membranes and blister recesses upon which to form interconnection channels. Because each side of the block has one layer allocated for blisters and another allocated for formation of interconnection channels, very complex valve interconnection schemes may be implemented in a small volume.

27 Claims, 4 Drawing Sheets

FLUID CONTROL VALVE ARRANGEMENT

CROSS-REFERENCE TO RELATED APPLICATIONS

This application relates to the co-pending application Ser. No. 08/709789, filed on the same day, entitled "ANALYTICAL ENGINE FOR GAS CHROMATOGRAPH", by Wylie, Raubvogel, and Leveson, owned by the assignee of this application and incorporated herein by reference.

BACKGROUND OF THE INVENTION

In gas chromatography and other fields, it is necessary to control the flow of one or more fluids by means of a system of control valves. The configuration of the system may be quite complex, and the valves themselves are often required to be very small and precise in operation. To meet this requirement, the internal volume of the valves should be very small.

Moreover, in many applications all surfaces which come into contact with the controlled fluid must be inert so as to avoid contaminating the fluid. Substances which react with or absorb the controlled fluid can seriously distort the results of a gas chromatography system, for example, since the required sensitivity of those results may be of the order of a few parts per billion, or even less.

It is desirable that the operation of the valves be as simple as possible and that the valves have a long service life (i.e., numerous openings and closures without failure). It is further desirable that valves and connecting channels be integrated into a single inert assembly which is easy to manufacture.

U.S. Pat. No. 4,353,243 to Martin, issued Oct. 12, 1982 describes an arrangement in which a plurality of diaphragm valves are linked by a peripheral channel formed in the surface of a solid plate. While useful in some applications, this system does not have the flexibility of being adaptable to extremely complex arrays and interconnections between a large number of valves.

U.S. Pat. No. 5,083,742 to Wylie, Leveson, Thomson, and Bray issued Jan. 28, 1992 and incorporated herein by reference, describes a fluid control valve for use with chemical fluids where avoidance of contaminants is important. The fluid control valve has a flow control chamber divided into an analytical section and a driver section by a metallic foil operating member, clamped between the peripheral rim of the chamber and the upper wall. The foil membrane is moveable in response to driver fluid pressure between open and closed positions. The upper portion of the rim which engages the membrane is of relatively small surface area, and is made of a softer material than that from which the membrane and the upper wall are constructed, thereby providing a very effective means of sealing the membrane periphery to the upper wall when the assembly is tightly clamped.

U.S. Pat. No. 5,176,359 to Leveson and Bassett, issued Jan. 5, 1993 and incorporated herein by reference, describes a plurality of clusters or pairs of holes extending from one face to the other of a central block selectively interconnected by grooves in the other face of the block. The valves comprise a plurality of blisters formed in a resilient membrane such that the blisters are positioned to coincide with the hole clusters when the membrane is pressed against the face of the block. However, the presence of both membrane sealing faces and grooves in the same block makes manufacturing and implementation of complex valve interconnection schemes more difficult because of the limited area available on the block.

SUMMARY OF THE INVENTION

A fluid control valve arrangement according to this invention comprises a block, a valve configuration and a seat plate to provide for separation of the valve configuration from the block surface. In accordance with this invention, passages comprising a plurality of channels and/or a plurality of holes are formed in a block, where some holes may be through-holes. Channels on the face of the block connect individual holes with other holes on the block resulting in an interconnection of passages. While in one embodiment the channels are substantially circular, the channels may have any shape and orientation convenient to connect individual holes with other holes on the block. The channels may have ridges to enhance sealing with the seat plate in contact with the face of the block. The seat plate has a plurality of through-holes arranged in clusters, with each cluster containing at least two holes, the holes communicating with the channels or holes in the block. The seat plate may have highly polished surfaces.

The face of the seat plate opposite to the face of the block is in contact with a resilient membrane (e.g., a thin sheet of steel) which has a plurality of blisters formed in it, the concave side of the blisters facing the respective seat plates. The blisters are positioned on a membrane so that each blister overlies a hole cluster in a seat plate. The hole clusters and blisters comprise one embodiment of the valves of this invention. The valves are similar to those described in U.S. Pat. No. 5,083,742 referenced above. The seat plate arrangement may also be used where other valve means, such as those disclosed in U.S. Pat No. 4,353,243 referenced above, are used to permit fluid flow through the hole clusters.

A drive plate is pressed firmly against the membrane, so as to deform the material of the block to prevent fluid from leaking among the holes and channels (see U. S. Pat. No. 5,083,742 to Wylie, Leveson, Thomson, and Bray referenced above). The drive plate has a plurality of recesses formed in it to contain the blisters. Each of the recesses is linked by a hole or a hole and a channel to a source of pressurized fluid. When pressurized fluid is admitted to the recess overlying a blister, the blister is pressed firmly against the seat plate, thereby sealing off communication between holes below the recess. This closes the valve. When the pressurized fluid is released, the blister springs back to its original shape, thereby opening the valve again. In the case where a reduced pressure is required beneath an "open" valve blister, it may be necessary to reduce the pressure above the blister to prevent the blister's collapse and the closing of the valve.

In one embodiment, there is a seat plate present on each face of the block with an accompanying valve membrane and drive plate. Because there are three layers of material between blister valve elements on opposite sides of the block, there are two interfaces on separate levels from those contacting valve membranes and blister recesses upon which to form interconnection channels. Because on each side of the block there is one interface allocated for blisters and another interface allocated for the formation of interconnection channels, very complex valve interconnection schemes can be implemented in a small volume. The sealing surfaces on either side of the seat plates do not require space to be allocated for interconnections. Hence, channels need only be formed in the relatively soft material of the block and not in the hard material of the seat plates. The drive plates may be formed of a relatively soft material as well to allow for easy fabrication. The block and drive plates are relatively soft because they need to be formed of a material having a lower yield strength than the seat plates to provide an effective seal with the seat plates.

DETAILED DESCRIPTION OF THE INVENTION

Figure 1:
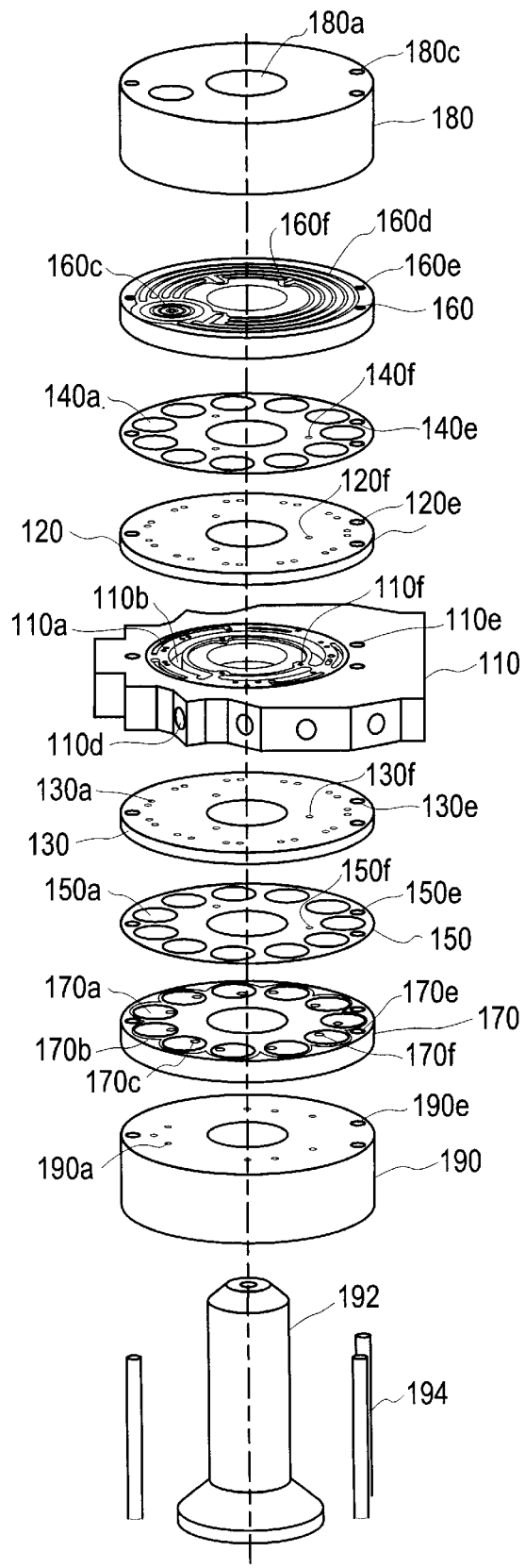
FIG. 1 shows an exploded view of one embodiment of a control valve arrangement in accordance with this invention.

FIG. 1 shows an exploded view of one embodiment of a control valve arrangement in accordance with this invention. This embodiment includes a central block 110, seat plates 120 and 130, membranes 140 and 150, drive plates 160 and 170, threaded bolt plate 180 and bolt plate 190, clamping bolt 192, and alignment pins 194.

In the embodiment shown, 28 holes 110a are formed in block 110. Here, there are 23 through-holes and 5 blind holes (non-through holes). Each blind hole and 8 of the through-holes communicate via 13 horizontal galleries with 13 ports 110d (see also FIG. 1a) at the edges of block 110. The galleries and the through-holes and blind holes may be formed in block 110 by drilling in from an edge or the upper or lower surface of block 110.

Figure 1A:
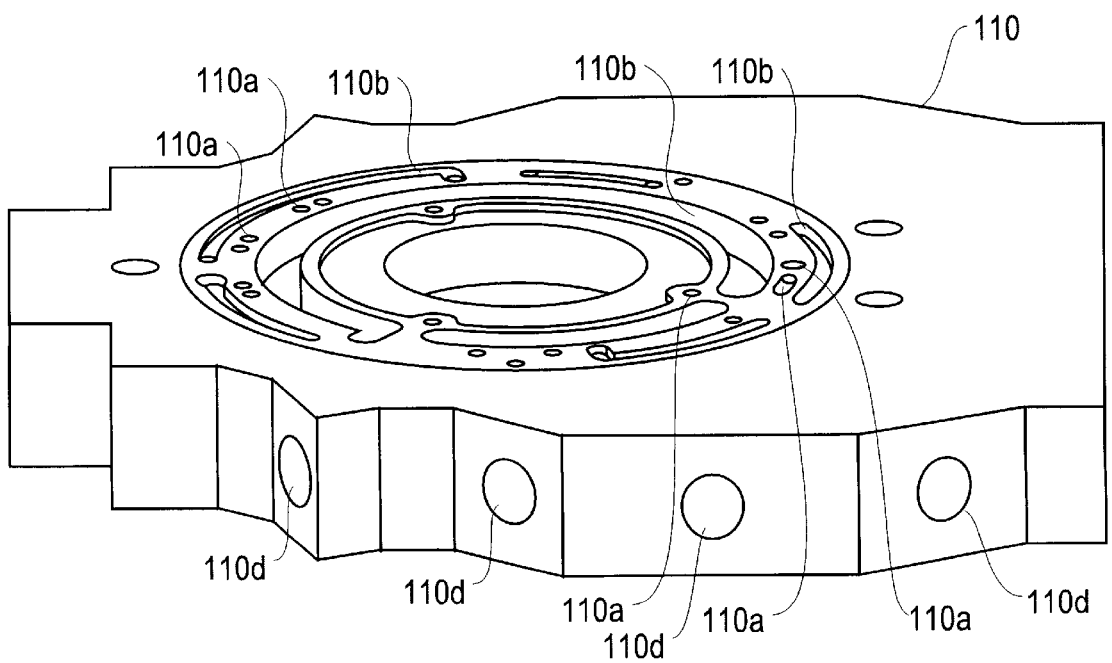
FIG. 1a shows a view of the block comprising passages and ports in an embodiment in accordance with this invention.

On the upper and lower surfaces of block 110, a series of channels 110b are formed (see also FIG. 1a). Channels 110b may be formed by milling. Galleries and channels may also be formed by casting. Channels 110b link individual holes 110a with other holes. In one embodiment 15 channels 110b are used, with 7 channels 110b being used on the upper surface of block 110 and 8 channels 110b being used on the lower surface of block 110. Channels 110b may also act as storage reservoirs for fixed volumes of fluid samples to be introduced into the fluid flow. In one embodiment, channels 110b have raised edges to allow plastic deformation of the material to create a seal when block 110 is pressed tightly against seat plates 120 and 130. Block 110 is preferably formed of a soft material such as elastomer, graphite fiber, polymer such as polyimide, or a soft metal such as aluminum and in one embodiment is polyether-ether-ketone (PEEK). Seat plates 120 and 130 have a plurality of through-holes 120a and 130a, respectively. Through-holes 120a and 130a are arranged in clusters such as, for example, in pairs and communicate with holes 110a or channels 110b formed in block 110. In one embodiment, 11 pairs of holes are present in each of seat plate 120 and 130. Seat plates 120 and 130 are preferably formed of a relatively hard material such as a metal, a ceramic, a hard polymer or a polymer composite and in one embodiment the seat plates are formed of stainless steel and are 1.5 inches in diameter. Having seat plates 120 and 130 formed of a relatively hard material enhances the seal with the ridges on block 110 made of a relatively soft material having a lower yield strength. The upper and lower faces of seat plates 120 and 130 are substantially parallel and each face of seat plates 120 and 130 is highly polished to enhance sealing with the raised edges of channels 110b in block 110 and with membranes 140 and 150. Membranes 140 and 150 are, for example, thin sheets of metal or a resilient polymer or elastomer and in one embodiment are made of "HAVAR" (an alloy of 42.5% cobalt, 13.0% nickel, 20% chromium, 17.8% iron and other metals at 2.8% or less) foil with a thickness of 0.0005 inch and a diameter of 1.45 inches. Membranes 140 and 150 have a plurality of blisters 140a and 150a formed or impressed into them. In one embodiment, membrane 140 has 10 blisters 140a while membrane 150 has 11 blisters 150a, the position of the 11th blister in membrane 140 being replaced by two holes. Each of blisters 140a and 150a has a concave surface facing seat plate 120 or seat plate 130 and a convex surface facing drive plate 160 or drive plate 170, respectively. Blisters 140a and 150a are positioned so that each of the blisters registers with a single pair of holes 120a or 130a. Membranes 140 and 150 must be thin and smooth enough to form a leakproof seal with the highly polished faces of seat plates 120 and 130, respectively. In addition, membranes 140 and 150 must be resilient enough to allow blisters 140a and 150a to be deformed repeatedly without affecting the blisters' ability to return to their original shape.

Moreover, where the controlled fluid must come into contact with only inert surfaces, seat plates 120 and 130, and membranes 140 and 150 should be made of a material such as, for example, stainless steel or, in particularly demanding applications, stainless steel coated with a highly inert material such as, for example, gold or glass. In these situations, block 110 can be made of an inert material such as, for example, polyether-ether-ketone (PEEK).

Membranes 140 and 150 are pressed against seat plates 120 and 130 by drive plates 160 and 170, respectively. A series of recesses 160a (see FIG. 2) and 170a are formed in drive plates 160 and 170, respectively. Recesses 160a and 170a coincide with the position of one of blisters 140a and 150a, respectively. Each of the recesses 160a and 170a forms a cavity, which allows each of blisters 140a and 150a to assume its normal shape when drive plates 160 and 170 are pressed firmly against seat plates 120 and 130, respectively. In one embodiment, each recess corresponding to a blister position is 0.250 inches in diameter and 0.005 inches in depth except for the two recesses corresponding to the two blisters where higher flow is required where the depth is 0.010 inches. Surrounding each of recesses 160a (see FIG. 2) and 170a on the surface of drive plates 160 and 170 is raised ring 160b (see FIG. 2) and raised ring 170b, respectively. When drive plates 160 and 170 press firmly against seat plates 120 and 130, rings 160b (not shown in FIG. 1., see FIG. 2 for location) and 170b press hard on membranes 140 and 150 thereby forming a particularly tight seal between membranes 140 and 150 and seat plates 120 and 130 around each pair of holes 120a and 130a, respectively. Each of recesses 160a and 170a contains apertures 160c and 170c which in one embodiment communicate with 3 channels 160d and 9 channels 170d (see FIG. 2), respectively.

In one embodiment, drive plates 160 and 170 have a diameter of 1.5 inches and are formed of PEEK and may also be formed of a soft material such as polymer, elastomer, graphite fiber or a soft metal such as copper. Channels 160d and 170d (see FIG. 2) in one embodiment have raised edges to enhance sealing with threaded bolt plate 180 and bolt plate 190, respectively. Bolt plates 180 and 190 are formed of 7075-T6 aluminum in one embodiment and provide support when drive plates 160 and 170, membranes 140 and 150, and seat plates 120 and 130 are pressed tightly against block 110.

The entire structure of FIG. 1 is clamped together by clamping bolt 192 which in one embodiment is made of alloy steel. Bolt 192 extends through the central hole in each member 190, 170, 150, 130, 110, 120, 140, 160, 180 (see FIG. 1) and fastens to threaded hole 180a in threaded bolt plate 180. Alignment of all members is maintained by alignment pins 194 which pass through and maintain an interference fit in corresponding holes 190e, 170e, 150e, 130e, 110e, 120e, 140e, 160e, 180e in each member. Alignment pins 194 in one embodiment are made of carbon steel.

Figure 3:
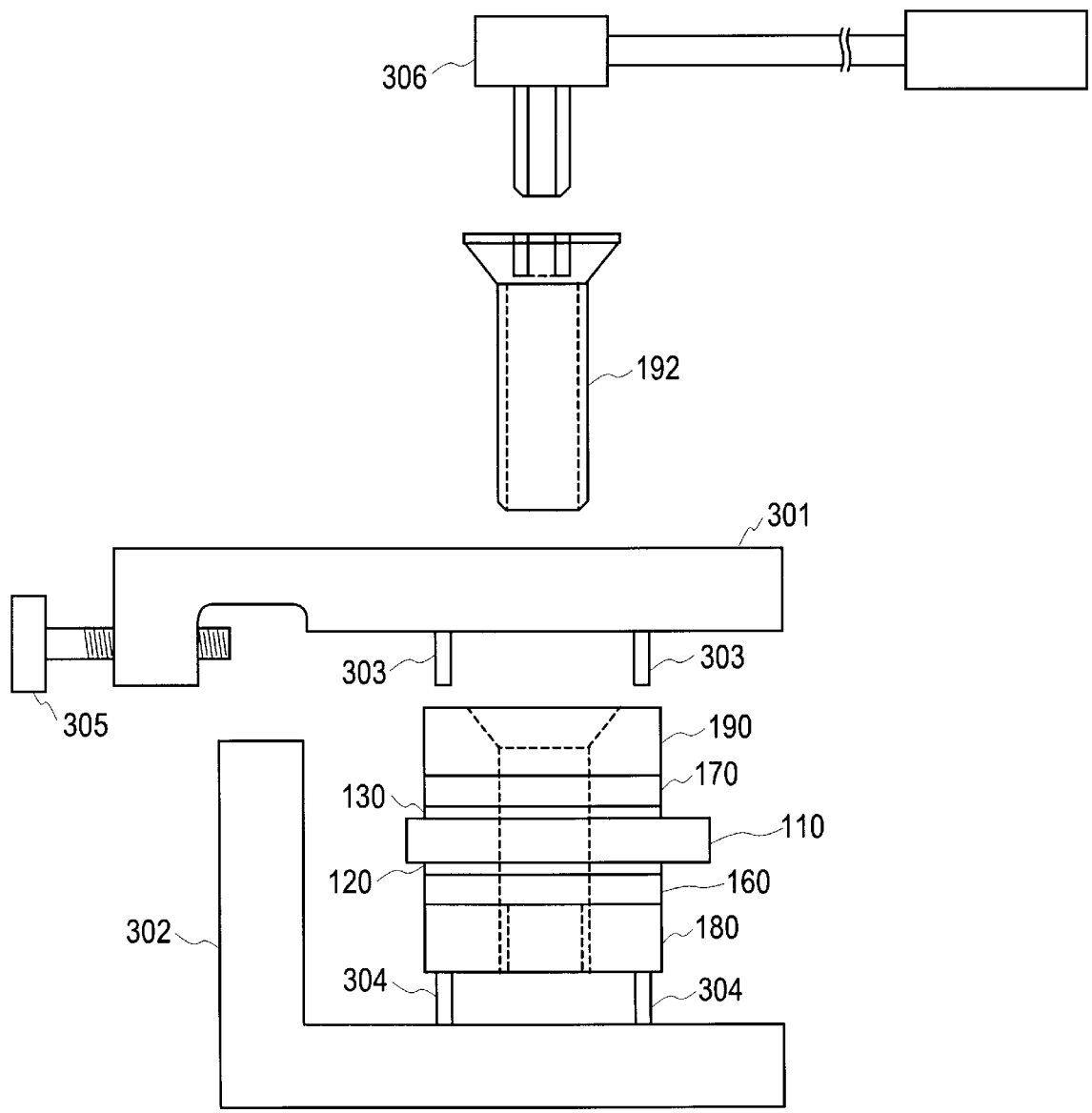
FIG. 3 shows the valve array assembly jig used to assemble the fluid control valve arrangement in one embodiment in accordance with this invention.

In one embodiment, the improved fluid control valve arrangement is assembled using the valve array assembly jig (see FIG. 3) to prevent misalignment of component parts of the improved fluid control valve arrangement. FIG. 3 shows the assembly jig composed of top 301 and base 302, top 301 having three protruding pins 303 and base 302 having three protruding pins 304 of hardened alloy steel. Top plate 301 has two thumbscrews 305 and 307 (not shown) to secure base 302 and top 301 together during the valve array assembly jig procedure. Torque wrench 306 applies the appropriate torque to clamping bolt 192. Base 302 is mounted securely to the assembly table. The assembly procedure is performed as described below.

Threaded bolt plate 180 is positioned on base 302 such that pins 304 protrude upwards from base 302 into holes 180e in threaded bolt plate 180. Alignment pins 194 are then placed into holes 180e from top of threaded bolt plate 180. The length of alignment pins 194 is given by the length of switching valve assembly 110 less the length of pins 304 and pins 303. Components 160, 140 (not shown in FIG. 3), 120, 110, 130, 150 (not shown in FIG. 3), 170, 190 are then stacked on threaded bolt plate 180. Top 301 is then placed on bolt plate 190 such that pins 303 protrude down into holes 190e in bolt plate 190. Thumbscrews 305 and 307 (not shown) are then tightened to secure top 301 to base 302. Clamping bolt 192 is then inserted through a hole in top 301 into bolt plate 190 through threaded bolt plate 180 and tightened. Torque wrench 306 is then applied to clamping bolt 192 to a torque of 60 ft lbs. Thumbscrews 305 and 307 (not shown) are then loosened, top 301 removed and the assembled fluid control valve arrangement is retrieved.

Figure 2:
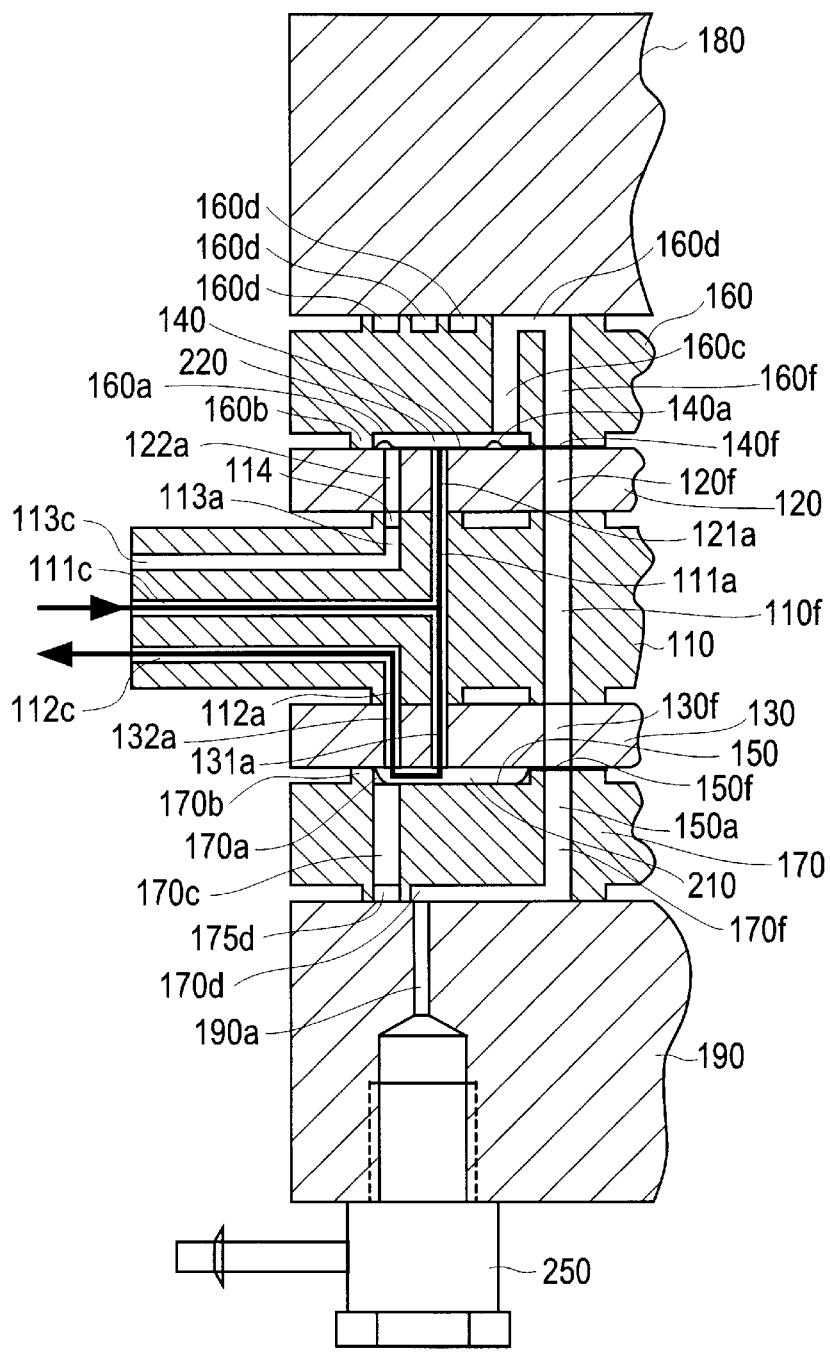
FIG. 2 shows a cross-sectional view of the construction of two valves in an embodiment in accordance with this invention.

In accordance with one embodiment of this invention, FIG. 2 shows a cross-sectional view of the construction of two valves, valve 210 and valve 220. Valve 220 includes the following elements: blister 140a, holes 121a and 122a in seat plate 120, recess 160a in drive plate 160 surrounded by ring 160b and holes 111a and 113a in plate 110. Valve 210 includes the following elements: blister 150a, holes 131a and 132a in seat plate 130, recess 170a in drive plate 170 surrounded by ring 170b and holes 111a and 112a in plate 110. The vertical dimensions of blisters 140a, blisters 150a, recesses 160a and recesses 170a are expanded in FIG. 2 for clarity. A height range for blisters 140a and blisters 150a of from 0.005 inches to 0.010 inches is found to yield satisfactory results. Channel 114 is oriented perpendicular to the plane of FIG. 2 and serves to connect hole 113a with other holes in block 110.

Channels 160d communicate with channels 170d via corresponding through-holes 160f and 170f in drive plates 160 and 170, through-holes 140f and 150f in membranes 140 and 150, through-holes 120f and 130f in seat plates 120 and 130, respectively, and through-hole 110f in block 110. In one embodiment, through-holes 160f and 170f in drive plates 160 and 170 have raised edges to enhance sealing with seat plates 120 and 130, respectively. Channels 170d and 175d further communicate through channels 190a and 195a (not shown, similar to 190a) in bolt plate 190 to driver fitting 250, so as to allow entry of a pressurized fluid such as nitrogen, for example, into recesses 160a and 170a.

Hole 111a (see FIG. 2), which is one of holes 110a (see FIG. 1), extends all the way through block 110 and allows communication between valve 210 and valve 220 (see FIG. 2) through holes 121a and 131a in seat plates 120 and 130, respectively. Horizontal galleries 111c, 112c and 113c formed in the interior of block 110 further allow communication between hole 111a and one of ports 110d (see FIG. 1) at an outside edge of block 110. The remaining holes 110a extend approximately half-way through block 110 and are joined by horizontal galleries (not shown) leading to ports 110d (see FIG. 1) at an outside edge of block 110.

When both valves 210 and 220 are open (as shown by valve 210 in FIG. 2) fluid is able to flow, for example, from gallery 112c on the bottom, through holes 112a on the bottom left, through hole 132a on the left, through valve 210, through holes 131a, 111a, and 121a, through valve 220, through hole 122a on the left, through hole 113a on the top left, into gallery 113c on the top. Fluid is also able to flow from hole 111a into middle gallery 111c.

Valve 220 is shown in closed position in FIG. 2. Valve 220 is closed by introducing a pressurized fluid, such as for example, nitrogen, from driver fitting 250 through hole 190a, through channel 170d on the right, through holes 170f, 150f, 130f, 110f, 120f, 140f, and 160f, through channel 160d on the right, through hole 160c, and into recess 160a. As shown in FIG. 2, the pressurized fluid forces flexible blister 140a downward against the aperture of hole 121a which is located centrally in valve 220. Blister 140a is pressed firmly against hole 121a, thereby closing off fluid flow through valve 220. When the pressurized fluid is released from recess 160a, blister 140a rebounds to its normal position, as shown by valve 210 in FIG. 2, thereby restoring fluid flow between pair of holes 121a and 122a and opening valve 220. Valve 210 is actuated by pressurized fluid going through channel 175d on the left.

FIG. 2 only shows a representative structure containing two valves 210 and 220 of one embodiment of the present invention. The structure can be expanded to encompass numerous valves which are linked by throughholes 110a and channels 110b (see FIGS. 1 and 1a) in any pattern or configuration required by a particular application.

Because interconnection channels 110b (see FIG. 1) are formed on the upper and lower faces of block 110 and because block 110 contacts neither membranes 140 and 150 nor blister recesses 160a and 170a, the entire sealing surface of seat plates 120 and 130 can be used for blisters. No additional lateral spacing is needed for the interconnections. Complex interconnection schemes may be implemented in a structure having a minimum diameter. The valves of the structure are extremely precise and responsive and can be manufactured with resilient membranes made of materials such as stainless steel which are capable of withstanding numerous deformations without fatigue or failure. Moreover, the valves may be designed so that the controlled fluid comes into contact with only inert surfaces and therefore suffers no contamination or degradation on passing through the valve structure. Types of valves other than those described herein can be used in accordance with this invention, such as those disclosed in U.S. Pat. No. 4,353,243 to Martin.

The various embodiments of the structure described above are merely illustrative and not intended to limit the scope of the invention to the particular embodiments described. In view of this disclosure, many additional and alternative embodiments according to the principles of this invention will be apparent to those skilled in the art.

We claim:

1. A fluid control valve arrangement comprising:
   a block having a first set of passages proximate a first face of said block;
   a seat plate, said seat plate having a plurality of clustered holes, said plurality of clustered holes of said seat plate extending from a first face of said seat plate to a second face of said seat plate, said second face of said seat plate pressed against said first face of said block; and
   a valve configuration positioned proximate said first face of said seat plate so as to control the flow of fluid through each of said plurality of clustered holes, said valve configuration comprising a membrane pressed against said first face of said seat plate, said membrane having a plurality of blisters, each of said blisters being permanently formed in said membrane, with a convex side and a concave side, and being positioned with said concave side thereof facing one of said plurality of clustered holes of said seat plate wherein individual ones of said blisters are deformable so as to prevent the flow of liquid through said plurality of clustered holes associated with said deformed blisters;
   wherein said plurality of clustered holes is in communication with said first set of passages; and
   wherein said block is made of a first material that is softer than a second material of which said seat plate is made from said block.

2. The fluid control valve arrangement of claim 1 further having a second set of passages proximate a second face of said block.

3. The fluid control valve arrangement of claim 1 comprising a drive plate for pressing said membrane against said first face of said seat plate, said drive plate including recesses which coincide with the respective locations of said blisters in said membrane.

4. The fluid control valve arrangement of claim 3 comprising a means for selectively deforming individual ones of said blisters.

5. The fluid control valve arrangement of claim 4 wherein said deforming means comprises means for selectively introducing a pressurized fluid into individual ones of said recesses.

6. The fluid control valve arrangement of claim 1 comprising a means for allowing a controlled fluid to flow into at least one of each said plurality of clustered holes and means for allowing said controlled fluid to flow out of at least another of each of said plurality of clustered holes.

7. A fluid control valve arrangement comprising:
   a block having a first set of passages proximate a first face of said block and ridges which surround individual ones of said first set of passages;
   a seat plate, said seat plate having a plurality of clustered holes, said plurality of clustered holes of said seat plate extending from a first face of said seat plate to a second face of said seat plate, said second face of said seat plate pressed against said first face of said block; and
   a valve configuration positioned proximate said first face of said seat plate so as to control the flow of fluid through each of said plurality of clustered holes, said valve configuration comprising a membrane pressed against said first face of said seat plate, said membrane having a plurality of blisters, each of said blisters being permanently formed in said membrane, with a convex side and a concave side, and being positioned with said concave side thereof facing one of said plurality of clustered holes of said seat plate wherein individual ones of said blisters are deformable so as to prevent the flow of liquid through said plurality of clustered holes associated with said deformed blisters;
   wherein said plurality of clustered holes is in communication with said first set of passages; and
   wherein said seat plate separates said valve configuration from said block.

8. The fluid control valve arrangement of claim 1 wherein said block comprises a face substantially perpendicular to both said first face of said block and said second face of said block, said face having at least one port.

9. The fluid control valve arrangement of claim 8 wherein said block contains a gallery, said gallery being in communication with said port and at least one of said first set of passages.

10. The fluid control valve arrangement of claim 3 wherein said drive plate contains a plurality of rings, each of said rings surrounding each of said plurality of clustered holes in said seat plate.

11. The fluid control valve arrangement of claim 3 wherein said drive plate is made of a third material, said third material being softer than said second material.

12. The fluid control valve arrangement of claim 11 wherein said material is selected from the group consisting of polyether-ether-ketone, graphite fiber, elastomer, a polymer such as polyimide, or a soft metal such as aluminum.

13. The fluid control valve arrangement of claim 1 wherein said seat plate and said membrane are made of an inert material.

14. The fluid control valve arrangement of claim 13 wherein said inert material is selected from the group consisting of stainless steel, a cobalt based alloy, a material coated with glass, and a material coated with gold.

15. A fluid control valve arrangement comprising:
    a block having a plurality of holes, individual ones of said plurality of holes of said block extending into an interior of said block from either a first face of said block or from a second face of said block and certain of said plurality of holes of said block extending from said first face of said block to said second face of said block, said first face of said block and said second face of said block each having channels linking certain of said plurality of holes of said block;
    a first seat plate, said first seat plate having a plurality of clustered holes, said plurality of clustered holes of said first seat plate extending from a first face of said first seat plate to said second face of said first seat plate, said second face of said first seat plate pressed against said first face of said block, a material of which said block is made being softer than a material of which said first seat plate is made;
    a second seat plate, said second seat plate having a plurality of clustered holes, said plurality of clustered holes of said second seat plate extending from a first face of said second seat plate to said second face of said second seat plate, said first face of said second seat plate pressed against said second face of said block;
    a first membrane pressed against said first face of said first seat plate, said first membrane having a plurality of blisters, each of said blisters being permanently formed in said membrane, with a convex side and a concave side, and being positioned with said concave side thereof facing one of said plurality of clustered holes of said first seat plate;

a second membrane pressed against said second face of said second seat plate, said second membrane having a plurality of blisters formed in it, each of said blisters being permanently formed in said membrane, with a convex side and a concave side, and being positioned with said concave side thereof facing one of said plurality of clustered holes of said second seat plate;

a first drive plate for pressing said first membrane against said first face of said first seat plate, said first drive plate including recesses which coincide with the respective locations of said blisters in said first membrane, the material of which said block is made being softer than a material of which said first drive plate is made;

a second drive plate for pressing said second membrane against said second face of said second seat plate, said second drive plate including recesses which coincide with the respective locations of said blisters in said second membrane;

wherein individual ones of said blisters are deformable so as to prevent the flow of fluid through said plurality of clustered holes associated with said deformed blisters.

16. The fluid control valve arrangement of claim 15 comprising means for allowing a controlled fluid to flow into at into at least one of each said plurality of clustered holes and means for allowing said controlled fluid to flow out of at least another of each said plurality of clustered holes.

17. The fluid control valve arrangement of claim 16 wherein said second seat plate, said first membrane and said second membrane are made of an inert material.

18. A fluid control valve arrangement comprising:

a block having a plurality of holes, individual ones of said plurality of holes of said block extending into an interior of said block from either a first face of said block or from a second face of said block and certain of said plurality of holes of said block extending from said first face of said block to said second face of said block, said first face of said block and said second face of said block each having channels linking certain of said plurality of holes of said block, said block containing ridges which surround individual ones of said channels;

a first seat plate, said first seat plate having a plurality of clustered holes, said plurality of clustered holes of said first seat plate extending from a first face of said first seat plate to said second face of said first seat plate, said second face of said first seat plate pressed against said first face of said block;

a second seat plate, said second seat plate having a plurality of clustered holes, said plurality of clustered holes of said second seat plate extending from a first face of said second seat plate to said second face of said second seat plate, said first face of said second seat plate pressed against said second face of said block;

a first membrane pressed against said first face of said first seat plate, said first membrane having a plurality of blisters, each of said blisters being permanently formed in said membrane, with a convex side and a concave side, and being positioned with said concave side thereof facing one of said plurality of clustered holes of said first seat plate;

a second membrane pressed against said second face of said second seat plate, said second membrane having a plurality of blisters formed in it, each of said blisters being permanently formed in said membrane, with a convex side and a concave side, and being positioned with said concave side thereof facing one of said plurality of clustered holes of said second seat plate;

a first drive plate for pressing said first membrane against said first face of said first seat plate, said first drive plate including recesses which coincide with the respective locations of said blisters in said first membrane; a second drive plate for pressing said second membrane against said second face of said second seat plate, said second drive plate including recesses which coincide with the respective locations of said blisters in said second membrane;

wherein individual ones of said blisters are deformable so as to prevent the flow of fluid through said plurality of clustered holes associated with said deformed blisters.

19. The fluid control valve arrangement of claim 18 wherein said block comprises a face substantially perpendicular to both said first face of said block and said second face of said block, said face having at least one port.

20. The fluid control valve arrangement of claim 19 wherein said block contains a gallery, said gallery being in communication with said port and at least one of said plurality of holes.

21. The fluid control valve arrangement of claim 15 wherein said first drive plate contains a plurality of rings, each of said rings surrounding each of said plurality of clustered holes in said first seat plate.

22. The fluid control valve arrangement of claim 15 wherein the material of which said block is made is softer than a material of which said second seat plate is made.

23. The fluid control valve arrangement of claim 22 wherein said material of which said block is made is selected from the group consisting of polyether-ether-ketone, graphite fiber, elastomer, a polymer such as polyimide, or a soft metal such as aluminum.

24. The fluid control valve arrangement of claim 15 comprising a means for selectively deforming individual ones of said blisters.

25. The fluid control valve arrangement of claim 24 wherein said deforming means comprises means for selectively introducing a pressurized fluid into individual ones of said recesses.

26. The fluid control valve arrangement of claim 15 wherein said first seat plate and said second drive plate have a substantially disklike shape.

27. The fluid control valve arrangement of claim 15 wherein said block has a substantially cylindrical shape.

* * * * *